(12) United States Patent
Okuda

(10) Patent No.: US 9,606,038 B2
(45) Date of Patent: Mar. 28, 2017

(54) PARTICLE COUNT MEASUREMENT DEVICE

(75) Inventor: Daiji Okuda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 198 days.

(21) Appl. No.: 14/402,611

(22) PCT Filed: May 21, 2012

(86) PCT No.: PCT/JP2012/062922
§ 371 (c)(1),
(2), (4) Date: Nov. 20, 2014

(87) PCT Pub. No.: WO2013/175548
PCT Pub. Date: Nov. 28, 2013

(65) Prior Publication Data
US 2015/0102822 A1 Apr. 16, 2015

(51) Int. Cl.
| | | |
|---|---|---|
| G01N 15/02 | (2006.01) | |
| G01N 27/62 | (2006.01) | |
| G01N 15/06 | (2006.01) | |
| B03C 3/017 | (2006.01) | |
| B03C 3/08 | (2006.01) | |

(Continued)

(52) U.S. Cl.
CPC ......... *G01N 15/0266* (2013.01); *B03C 3/017* (2013.01); *B03C 3/08* (2013.01);
(Continued)

(58) Field of Classification Search
CPC ........... G01N 15/0656; G01N 15/0266; G01N 1/2252; G01N 27/70; G01N 30/64;
(Continued)

(56) References Cited

U.S. PATENT DOCUMENTS

| 3,718,029 A | 2/1973 | Gourdine et al. |
| 4,531,402 A * | 7/1985 | Reif .................. G01N 15/0266 324/454 |

(Continued)

FOREIGN PATENT DOCUMENTS

| JP | 05-049970 A | 3/1993 |
| JP | 2006-250576 A | 9/2006 |

(Continued)

OTHER PUBLICATIONS

Extended Supplementary European Search Report dated Dec. 18, 2015, issued in counterpart European Patent Application No. 12877345.4 (10 pages).

(Continued)

*Primary Examiner* — Alesa Allgood
(74) *Attorney, Agent, or Firm* — Westerman, Hattori, Daniels & Adrian, LLP

(57) ABSTRACT

A particle count measurement device includes a preprocessing section configured to place an aerosol introduced into a measurement region in an electrical state of any of a neutralized state, a positively charged state or a negatively charged state, a unipolar charging section configured to place the aerosol which has been introduced in an electrical state different from at a time of introduction, an ion trap arranged on a downstream of the unipolar charging section in terms of a flow of the aerosol for generating an electric field that draws only gas ions in the aerosol, an exhaust mechanism configured to discharge the aerosol from the measurement region at a constant flow rate, and an ammeter for detecting, as a measurement value corresponding to a particle count concentration, a difference between current supplied by the unipolar charging section and current flowing into the ion trap.

9 Claims, 7 Drawing Sheets

(51) Int. Cl.
*B03C 3/12* (2006.01)
*B03C 3/38* (2006.01)
*B03C 3/41* (2006.01)
*B03C 3/47* (2006.01)
*G01N 15/00* (2006.01)

(52) U.S. Cl.
CPC ............ *B03C 3/12* (2013.01); *B03C 3/38* (2013.01); *B03C 3/41* (2013.01); *B03C 3/47* (2013.01); *G01N 15/0656* (2013.01); *G01N 27/62* (2013.01); *B03C 2201/06* (2013.01); *B03C 2201/24* (2013.01); *G01N 2015/0038* (2013.01)

(58) Field of Classification Search
CPC ........ G01N 27/62; G01N 27/66; G01N 27/68; G01N 2030/642; G01N 27/64; G01N 27/622; G01N 2015/0038; H01T 23/00; B03C 3/38; B03C 3/12; H01J 49/168; H01J 37/32935; B01J 19/125; B05D 1/06; H01L 21/67028; H05H 1/0081
See application file for complete search history.

(56) References Cited

U.S. PATENT DOCUMENTS

| | | | |
|---|---|---|---|
| 6,991,045 B2 * | 1/2006 | Vinegar | .................. B09C 1/02 166/66.5 |
| 7,066,037 B2 | 6/2006 | Keskinen et al. | |
| 2006/0156791 A1 | 7/2006 | Tikkanen et al. | |
| 2011/0050243 A1 * | 3/2011 | Tikkanen | ............. G01N 1/2252 324/464 |

FOREIGN PATENT DOCUMENTS

| | | |
|---|---|---|
| JP | 2007-514923 A | 6/2007 |
| JP | 2011-513742 A | 4/2011 |
| WO | 2009/109688 A1 | 9/2009 |

OTHER PUBLICATIONS

International Search Report dated Aug. 7, 2012, issued in corresponding application No. PCT/JP2012/062922.

* cited by examiner

PARTICLE COUNT MEASUREMENT DEVICE

TECHNICAL FIELD

The present invention relates to a device for measuring the particle count in an aerosol, and for example, relates to a device for mainly measuring the particle count of particles that are about 100 nm or smaller. An aerosol is a colloid whose dispersion medium is gas, and whose dispersoid is liquid or solid. When the dispersoid is liquid, the aerosol is fog, mist, cloud or the like, and when the dispersoid is solid, it is dust, smoke or the like.

Measurement of elemental components of fine particles in the aerosol has a significant meaning in the research related to evaluation of the environmental state, health effect and the like. As the measurement of the aerosol, there is, for example, air pollution measurement. Exhaust gas from the combustion engine of a vehicle and flue gas from an industrial plant which cause environmental pollution or air pollution in recent years include sulfur compounds ($SO_x$, $H_2S$, etc.), nitrogen compounds ($NO_x$, $NH_3$, etc.), hydrocarbons, and the like, and these turn into hydrosulfate or nitrate by chemical reaction or photochemical reaction, absorb the water vapor in the air, and become a liquid aerosol.

BACKGROUND ART

As the technique for measuring the particle count or the approximate number of particle masses in an aerosol, a method of charging particles, measuring the charge amount of the particles as a current value, and estimating the amount of particles based on the correlation coefficient between the current value and the particle count or the surface area of the particles is known, and a device for carrying out the method is already in the market. This method is characteristic in that, compared to other methods, highly sensitive measurement may be easily performed by a simple structure with respect to small particles with diameters of 100 nm or less.

This method includes two modes.

(a) The first mode is for positively or negatively charging particles (aerosol) in a gaseous phase by DC corona discharge or the like and collecting the charged particles on an electrode, and measuring a charge amount thereof as a current value. Then, the particle count or the particle surface area is estimated based on a relational expression between current and the particle count or between current and the particle surface area prepared in advance (see Patent Documents 1 and 2).

(b) The second mode is developed as an improvement of the first mode. According to the second mode, particles are not collected after being charged, and the charge amount removed from a spatial region by the charged particles is measured as the current (see Patent Document 3). This mode is characteristic in that, since the charged particles do not have to be collected, maintenance of a detection section is easy.

As a typical method, the second mode ionizes the air by high voltage DC discharge and mixes the generated unipolar ions with the particles in an aerosol to thereby charge the particles by diffusion. Then, when a flow including the charged particles passes through a space, a predetermined electric field is applied to the space, and gas ions smaller than the particles are collected and removed. On the other hand, the charged particles which are not collected in the space move out of the spatial region. The charge amount that is moved out by the charged particles from the spatial region at that time is measured.

PRIOR ART DOCUMENTS

Patent Documents

Patent Document 1: U.S. Pat. No. 7,066,037
Patent Document 2: US 2006/0156791
Patent Document 3: WO 2009/109688 A

SUMMARY OF THE INVENTION

Problems to be Solved by the Invention

The present invention relates to improvement of the second mode described above. According to the second mode, the difference between the charge amount flowing into a measurement device and the charge amount flowing out of the measurement device is measured, and thus, the amount of particles which were charged before flowing into the measurement device is not measured. Therefore, if the charged amount of the particles flowing in is not known, accurate measurement cannot be performed.

The present invention has its aim to enable accurate measurement of the particle count in an aerosol which is the target of measurement, even if the aerosol which is the target of measurement includes particles which were charged before flowing into a measurement device, and even if the charged amount of the charged particles is unknown.

Solutions to the Problems

The present invention is a particle count measurement device for measuring a particle count concentration of an aerosol flowing through a measurement region, the particle count measurement device including a preprocessing section configured to place the aerosol introduced into the measurement region in an electrical state of any of a neutralized state, a positively charged state or a negatively charged state, a unipolar charging section inside the measurement region, the unipolar charging section being configured to place the aerosol which has been introduced in either a positively charged state or a negatively charged state that is an electrical state different from at a time of introduction into the measurement region, an ion trap arranged inside the measurement region, on a downstream of the unipolar charging section in terms of a flow of the aerosol, the ion trap including an ion trap electrode for generating an electric field that draws only gas ions in the aerosol, an exhaust mechanism outside the measurement region, the exhaust mechanism being configured to discharge the aerosol from the measurement region at a constant flow rate, and an ammeter for detecting, as a measurement value corresponding to the particle count concentration, a difference between current supplied by the unipolar charging section and current flowing into the ion trap. The particle count concentration of the aerosol flowing through the measurement region per unit time is measured based on the measurement value of the ammeter.

According to a first aspect of the present invention, the preprocessing section is a neutralizer, and the particle count concentration of particles that are neutralized by causing the total of the charge amount of particles in the aerosol flowing into the measurement region from the inlet to be substantially zero at all times, that are introduced into the measurement region, that are positively or negatively charged, and that are then made to flow out of the measurement region is measured. According to a more concrete example of this case, the preprocessing section is a discharge neutralizer for placing the aerosol in a neutralized state by AC corona discharge, and the unipolar charging section is a discharge charger based on unipolar corona discharge, the discharge charger including a DC high-voltage power supply and an electrode.

According to a second aspect of the present invention, the preprocessing section is a positive charger that performs positive DC discharge, and positively charges the particles in the aerosol flowing into the measurement region from the inlet, and then, the particles in the aerosol are negatively charged at the unipolar charging section. In this case, the particles in the aerosol flow into the measurement region being positively charged, and flow out of the measurement region being negatively charged, and the particle count concentration is thus measured based on the charge amount of the difference. According to a more concrete example of this case, the preprocessing section is a discharge charger for placing the aerosol in a positively charged state by positive DC corona discharge, and the unipolar charging section is a discharge negative charger based on negative unipolar corona discharge, the discharge negative charger including a negative DC high-voltage power supply and an electrode.

In a third aspect of the present invention, the charge state is opposite that of the second aspect. That is, the preprocessing section is a negative charger that performs negative DC discharge, and negatively charges the particles in the aerosol flowing into the measurement region from the inlet, and then, the particles in the aerosol are positively charged at the unipolar charging section. In this case, the particles in the aerosol flow into the measurement region being negatively charged, and flow out of the measurement region being positively charged, and the particle count concentration is thus measured based on the charge amount of the difference. According to a more concrete example of this case, the preprocessing section is a discharge charger for placing the aerosol in a negatively charged state by negative DC corona discharge, and the unipolar charging section is a discharge positive charger based on positive unipolar corona discharge, the discharge positive charger including a positive DC high-voltage power supply and an electrode.

According to a preferred embodiment, the exhaust mechanism includes a flow rate adjustment section for making an exhaust flow rate constant. No particular restriction is imposed on the flow rate adjustment section as long as the flow rate may be made constant, and a critical orifice, an adjustment valve, a flowmeter, a mass flow controller or the like may be used. In the case of the critical orifice, the structure is simplified. The critical orifice is an orifice through which air passes at the speed of sound, and the mass flow rate injected from the critical orifice is determined based on the size of the orifice, and the absolute pressure and the absolute temperature on the upstream side.

Regarding monitoring of the particle count concentration in an aerosol, if exhaust gas of, for example, a combustion engine is the measurement target, the mass flow rate inside the exhaust duct is not constant, and is dependent on the rotational speed of the engine. In such a case, if the exhaust mechanism includes the flow rate adjustment section for making the exhaust flow rate constant, the measurement target gas flows at a constant mass flow rate through the measurement region where the particle count concentration is measured, and the particle count concentration may be stably measured as well.

According to another preferred embodiment, a diffusion filter arranged between the ion trap and an outlet of the measurement region and formed from a conductive mesh for removing charged particles of particle diameters smaller than a predetermined particle diameter is further provided. In this case, the ammeter may measure a particle count concentration of particles having particle diameters equal to or greater than the predetermined particle diameter by measuring a difference between current supplied by the unipolar charging section and total current flowing into the ion trap and the diffusion filter.

According to yet another preferred embodiment, a pair of counter electrodes and a classification power supply are provided. The pair of counter electrodes are arranged between the ion trap and an outlet of the measurement region in parallel with a flow of an aerosol. The classification power supply is to generate, at the counter electrodes, an electric field for drawing charged particles having particle diameters smaller than a predetermined particle diameter. In this case, the ammeter may measure a particle count concentration of particles having particle diameters equal to or greater than the predetermined particle diameter by measuring a difference between current supplied by the unipolar charging section and total current flowing into the ion trap and the counter electrodes.

According to yet another preferred embodiment, a pair of counter electrodes, a classification power supply and a classification ammeter are provided. The pair of counter electrodes are arranged between the ion trap and an outlet of the measurement region in parallel with a flow of an aerosol. The classification power supply is to generate, at the counter electrodes, an electric field for drawing charged particles having particle diameters smaller than a predetermined particle diameter. The classification ammeter is to measure current flowing into the counter electrodes. In this case, a particle count concentration of particles having particle diameters greater than the gas ions but smaller than the predetermined particle diameter may also be measured based on a measurement value of the classification ammeter.

In this case, if voltage is applied to the ion trap electrode of the ion trap so as to generate an electric field that draws not only the gas ions in the aerosol, but also charged particles of particle diameters smaller than the predetermined particle diameter, a particle count concentration of particles having particle diameters in a specific range which is greater than particle diameters to be captured by the ion trap electrode and is smaller than the predetermined particle diameter may be measured.

Effects of the Invention

According to the present invention, by causing the charged state of particles in an aerosol that is introduced into a measurement region where current is to be measured to be constant by the preprocessing section, the amount of particles may be correctly measured without being influenced by the original charged state of the particles in the aerosol. Although the charged state of target particles changes depending on the composition or the generation mechanism of the measurement target particles, reproducible measurement not depending on the initial charged state of the particles is enabled by the present invention, and highly accurate measurement may be performed for various types of aerosols.

Furthermore, the particle count measurement device of the present invention may perform measurement with no regard to whether or not a measurement target aerosol includes particles which were charged before flowing into the measurement region.

EMBODIMENTS OF THE INVENTION

Figure 1:
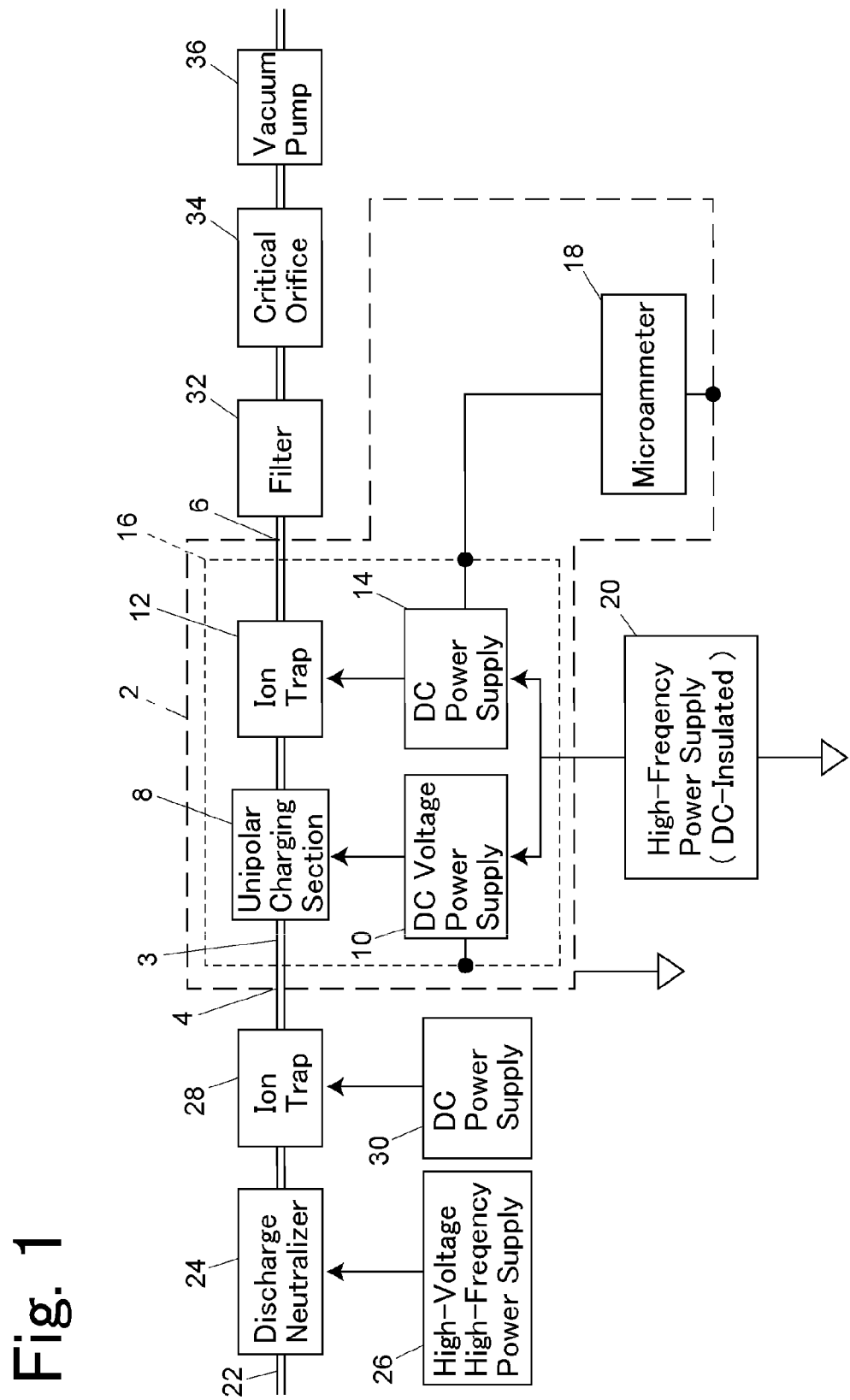
FIG. 1 is a block diagram schematically showing an embodiment.

FIG. 1 is a block diagram schematically showing an embodiment. A shield electrode 2 is provided to form a spatial region for measurement of particle count concentration in a measurement target aerosol, and the spatial region is surrounded by the shield electrode 2. The shield electrode 2 is formed of conductive material, and is grounded so as not to be influenced by electromagnetic waves from outside. The spatial region surrounded by the shield electrode 2 is a measurement region where the difference between flow-in and flow-out of charged particles is to be measured.

A flow path 3 through which a measurement target aerosol flows through the measurement region. A unipolar charging section 8 for charging the aerosol introduced from an inlet 4 positioned at the boundary of the measurement region is arranged on the flow path 3. A DC high-voltage power supply 10 is connected to an electrode of the unipolar charging section 8, and positive potential or negative potential is applied by the high-voltage power supply 10 in such a way that corona discharge is generated by the electrode of the unipolar charging section 8. In the present embodiment, to apply positive potential, the high-voltage power supply 10 applies positive voltage of about 2 KV to 10 KV on the electrode of the unipolar charging section 8. At the unipolar charging section 8, gas molecules in the aerosol (specifically, nitrogen molecules and oxygen molecules) are ionized by the discharge from the electrode and gas ions are generated, and the generated gas ions come into contact with the particles in the aerosol to charge the particles. In this example, the particles are positively charged.

In the measurement region, an ion trap 12 is arranged on the downstream of the unipolar charging section 8 along the flow direction of the aerosol in the flow path 3. A DC power supply 14 is connected to an electrode of the ion trap 12, and an electric field of the opposite polarity from the unipolar charging section 8 is applied. Among the charged particles flowing through the flow path 3 in the measurement region 2, the gas ions have high electrical mobility and are easily trapped by a small electric field, and are thus captured by the ion trap 12. On the other hand, particles of, for example, about 5 nm or larger have low electrical mobility compared to the gas ions and are, therefore, hardly captured by the ion trap 12, and flow out, along the flow of the gas, from a flow path outlet 6 that is at the boundary of the measurement region. The magnitude of the electric field at the ion trap 12 is set in such a way that only the gas ions are captured and charged particles other than the gas ions freely pass through without being captured. In the present embodiment, the DC power supply 14 applies negative voltage of about 1 to 100 V to the electrode of the ion trap 12 so that negative potential is applied to the electrode of the ion trap 12. At the ion trap 12, the gas ions remaining in the aerosol, among the gas ions generated by the unipolar charging section 8, are captured by the electrode of the ion trap 12.

The unipolar charging section 8, the DC high-voltage power supply 10, the ion trap 12, and the DC power supply 14 are arranged inside the shield electrode 2 so as to avoid influence of disturbance.

In the measurement electrode, a guard electrode 16 for measuring entering and leaving of charged particles into and from the shield electrode 2 is provided, and a microammeter 18 provided inside the shield electrode 2 is connected to the guard electrode 16 to measure the entering and leaving of the charged particles. A flow path portion 3*a* inside the shield electrode 2 may be used also as the guard electrode 16, as in the embodiment shown in FIGS. 2 and 3 described later.

The DC high-voltage power supply 10 and the DC power supply 14 are supplied with energy by alternating current from a high-frequency power supply 20, and are insulated for DC voltage. This is to accurately measure the value of micro current carried by the charged particles. Details will be given in the description of FIG. 2 given later.

A COM line of the DC high-voltage power supply 10 and the DC power supply 14 arranged inside the shield electrode 2 is connected to the guard electrode 16, and the microammeter 18 measures the current between the guard electrode 16 and the shield electrode 2. That is, the microammeter 18 is to measure the current value of the charge particles charged at the unipolar charging section 8 and carried out of the measurement region surrounded by the shield electrode 2.

To make the aerosol to be introduced into the measurement region carry no charge, a discharge neutralizer 24 is arranged as a preprocessing section in a portion between an aerosol supply port 22 and before entering of the measurement region so as to neutralize the aerosol. A high-voltage high-frequency power supply 26 is connected to an electrode of the neutralizer 24, and by generating positive gas ions and negative gas ions from the air in the aerosol, the charge of the particles in the aerosol, including originally charged particles included in the aerosol, is neutralized. Voltage of 2 to 10 KV is applied at 50 Hz to 1 MHz to the electrode of the neutralizer 24 by the high-voltage high-frequency power supply 26.

An ion trap 28 is provided in a portion between the neutralizer 24 and before entering of the region of the shield electrode 2 for removing gas ions remaining after neutralization. The ion trap 28 is provided with a pair of electrodes, and an electric field is applied between the electrodes by a DC power supply 30. Gas ions are captured by the electrodes by the electric field, and a state is achieved where there are no remaining gas ions in the aerosol to be supplied to the measurement region. If neutralization is ideally performed by the neutralizer 24, the ion trap 28 would not be necessary, but in reality, gas ions will remain. If remaining gas ions enter the measurement region, these will become noise current, and thus, the ion trap 28 is desirably provided.

Voltage of 1 to 100 V is applied between the pair of electrodes of the ion trap 28 by the DC power supply 30.

Outside the measurement region and on the downstream of the flow path 3, a vacuum pump 36 for drawing the aerosol into the measurement region is arranged. Between the flow path outlet 6 positioned at the boundary of the measurement region and the vacuum pump 36, a filter 32 for removing particles in the aerosol and a critical orifice 34 for causing gas from which particles have been removed to flow at a constant flow rate are arranged from the outlet 6 side. The flow rate of aerosol to be introduced into the measurement region is controlled to be constant by the critical orifice 34 and the vacuum pump 36. The diameter of the orifice of the critical orifice 34 is, for example, 100 to 500 µm and the flow rate is set to be, for example, about 1 to 10 L per minute.

According to the present embodiment, by providing the neutralizer 24, the aerosol to be introduced into the measurement region is neutralized. When neutralized particles flow into the guard electrode 16, positively charged gas ions are generated by discharge at the unipolar charging section 8 by the high-voltage power supply 10. These gas ions attach, by being diffused, to the particles which have flown in to charge the particles. Since an appropriate DC electric field is applied at the ion trap 12 on the downstream, the remaining gas ions after neutralization are captured and collected, but most particles with diameters of, for example, about 5 nm or more flow further downstream without being captured. As a result, by Kirchhoff's law, the current flowing into the microammeter 18 via the guard electrode 16 becomes equal to the amount of current carried outside the guard electrode 16 by the charged particles.

In the present embodiment, the gas flow rate is controlled by the critical orifice 34 and the vacuum pump 36 to be a constant flow rate, and thus, the charged amount of particles in a unit volume is calculated based on the flow rate and the value of current measured by the microammeter 18.

Conversion from the charged amount to the amount of particles is dependent on the charging characteristics of the particles including the characteristics of a charging device, but by experimentally determining the conversion coefficient for the conversion in advance, the particle count estimation value may be obtained in real-time.

In the present embodiment, both the neutralizer 24 and the unipolar charging section 8 use corona discharge, and there is no risk of radiation damage as in the case of using a radiation charger.

Since the critical orifice 34 is used to make the flow rate of a sample flowing through the measurement region constant, the flow rate may be stabilized by a structure which is simple when compared to a flow rate adjustment mechanism such as a mass flow controller.

Figure 2:
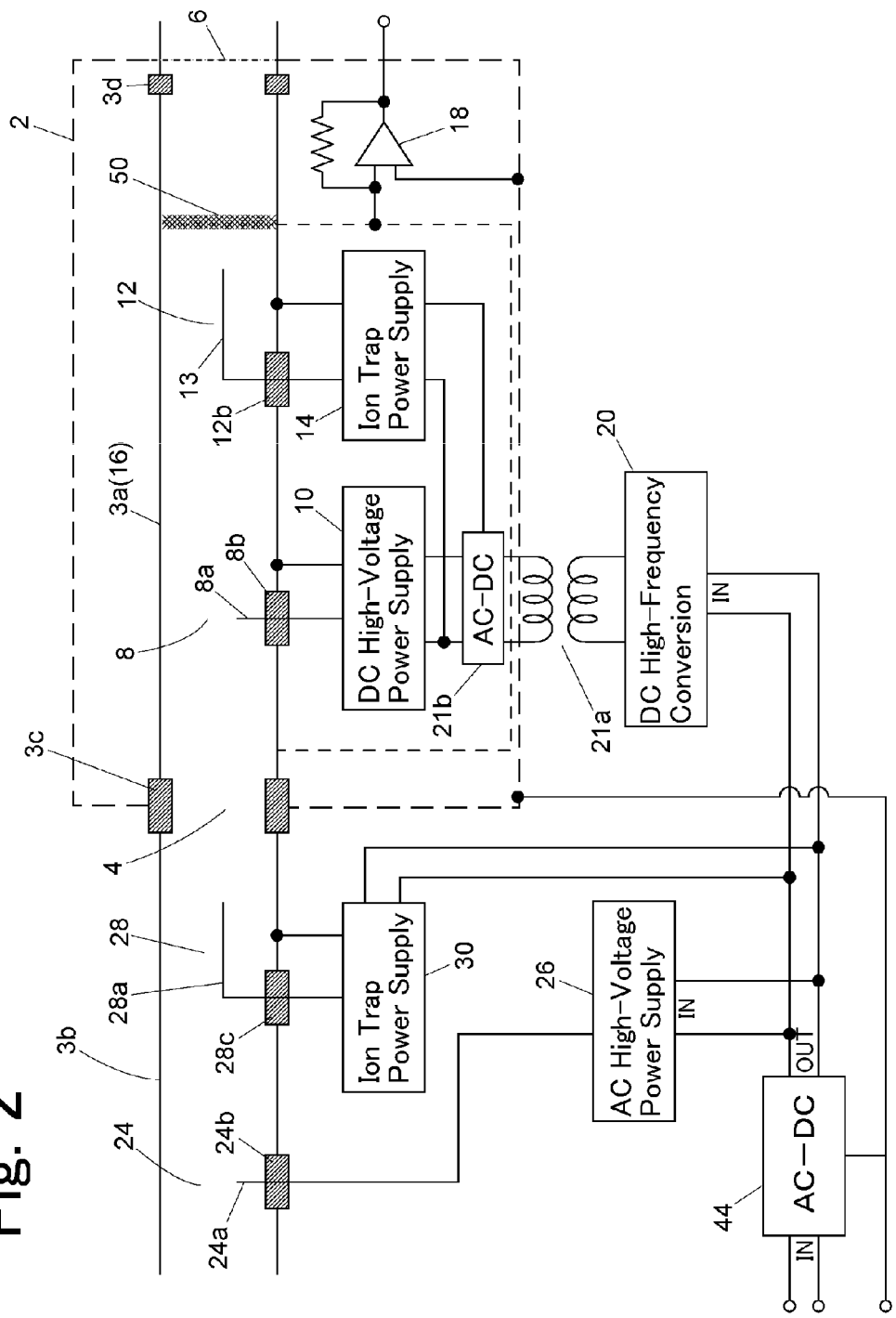
FIG. 2 is a circuit diagram showing the embodiment.

FIG. 2 shows the configuration of the embodiment in more detail.

The flow path 3 is cylindrical, and is formed of conductive material. The flow path 3 includes a portion 3a inside the measurement region, and a portion 3b of the preprocessing section on the inlet side where the discharge neutralizer 24 is arranged. The portions 3a and 3b are electrically separated by a ring-shaped insulating member 3c. At the neutralizer 24, to perform neutralization by AC corona discharge, an electrode 24a is connected to the AC high-voltage power supply 26. The electrode 24a is attached inside the flow path 3b while being insulated from the flow path 3b by an insulating member 24b. At the ion trap 28, an electrode 28a is attached inside the flow path 3b while being insulated from the flow path 3b by an insulating member 28c. By the DC power supply 30 for supplying ion trap power being connected between the electrode 28a and the flow path 3b, the flow path 3b is the other electrode of the ion trap 28. An electric field for the ion trap is applied between the electrode 28a and the flow path 3b.

An electrode 8a of the unipolar charging section 8 is attached inside the flow path 3a while being insulated from the flow path 3a by an insulating member 8b. An electrode 13 of the ion trap 12 is also attached inside the flow path 3a while being insulated from the flow path 3a by an insulating member 12b. The flow path 3a is electrically separated on the inside and the outside of the measurement region by a ring-shaped insulating member 3d at a boundary portion on the downstream side of the measurement region. The flow path 3a serves also as the guard electrode 16.

A terminal on the positive electrode side of the DC high-voltage power supply 10 is connected to the electrode 8a of the unipolar charging section 8, a terminal on the negative electrode side of the ion trap power supply 14 is connected to the electrode 13 of the ion trap 12, and the COM line of the power supplies 10 and 14 is connected to the flow path 3a configuring the guard electrode 16.

Power is supplied to the high-voltage power supply 10 of the unipolar charging section 8 from a DC-high frequency conversion circuit 20 provided outside the shield electrode 2 via a transformer 21a and an AC-DC converter 21b. Power is similarly supplied to the DC power supply 14 for the ion trap via the transformer 21a and the AC-DC converter 21b. It is important that, with respect to the transformer 21a, the leakage of direct current is small. Thus, the DC-high frequency conversion circuit 20 is installed inside a shield case, the shield case and the circuit COM of the DC-high frequency conversion circuit 20 are connected to the flow path 3a, and the transformer 21a is also installed inside the shield case, and the shield case of the transformer 21a is connected to the flow path 3a. To suppress current leakage, it is desirable that a material is selected for the transformer 21a in such a way that the DC resistance between a primary circuit and a second circuit is about 1000 TΩ or more, and that a sufficient creepage distance is maintained. Moreover, to prevent reduction in impedance due to moisture or dust, the transformer 21a is desirably accommodated in an airtight container, and the inside of the container is desirably kept dry.

To supply power to the AC high-voltage power supply 26 and the DC-high frequency conversion circuit 20, DC power is supplied by an AC-DC converter 44. A battery may be used instead of the AC-DC converter 44. If a battery is used, leakage of direct current may be easily coped with.

The microammeter 18 including a current-voltage conversion circuit is connected between the flow path 3a serving also as the guard electrode 16 and the shield electrode 2. The output of the microammeter 18 is extracted and is converted into a particle count or the particle surface area.

A diffusion filter 50 may be provided inside the flow path 3 near the outlet 6 inside the measurement region. The diffusion filter serves to limit the range of diameters of particles that flow out to, for example, about 20 nm or more. A conductive mesh may be provided in the flow path and be connected to the guard electrode 16 to realize the diffusion filter 50.

The relationship between the mesh size and the diameter of a charged particle to be captured by the mesh may be stated as below.

The Brownian motion of particles is great when the particle diameter is several tens of nm or less, and thus, capturing is facilitated as the particle diameter is smaller. In a simple model of a case where fibrous collecting bodies are placed in a laminar flow, gaps between fibers are assumed to be "microcylinders". In this case, the capture rate η of a single cylinder is expressed by the following equation.

$$\eta = 2.9k^{(-1/3)} \times Pe^{(-2/3)} + 0.62 Pe^{(-1)}$$

where $$k = -0.5 Ln(\alpha) - (3/4) + \alpha - \alpha^2/4 \text{ (in the case of parallel cylinder group)},$$

α is the filling rate (the proportion of the microcylinders to the flow path), and Pe is a Peclet number, where Pe=2UR/D (U is the flow velocity, R is the radius of the microcylinder, and D is a Brownian diffusion coefficient).

Figure 3:
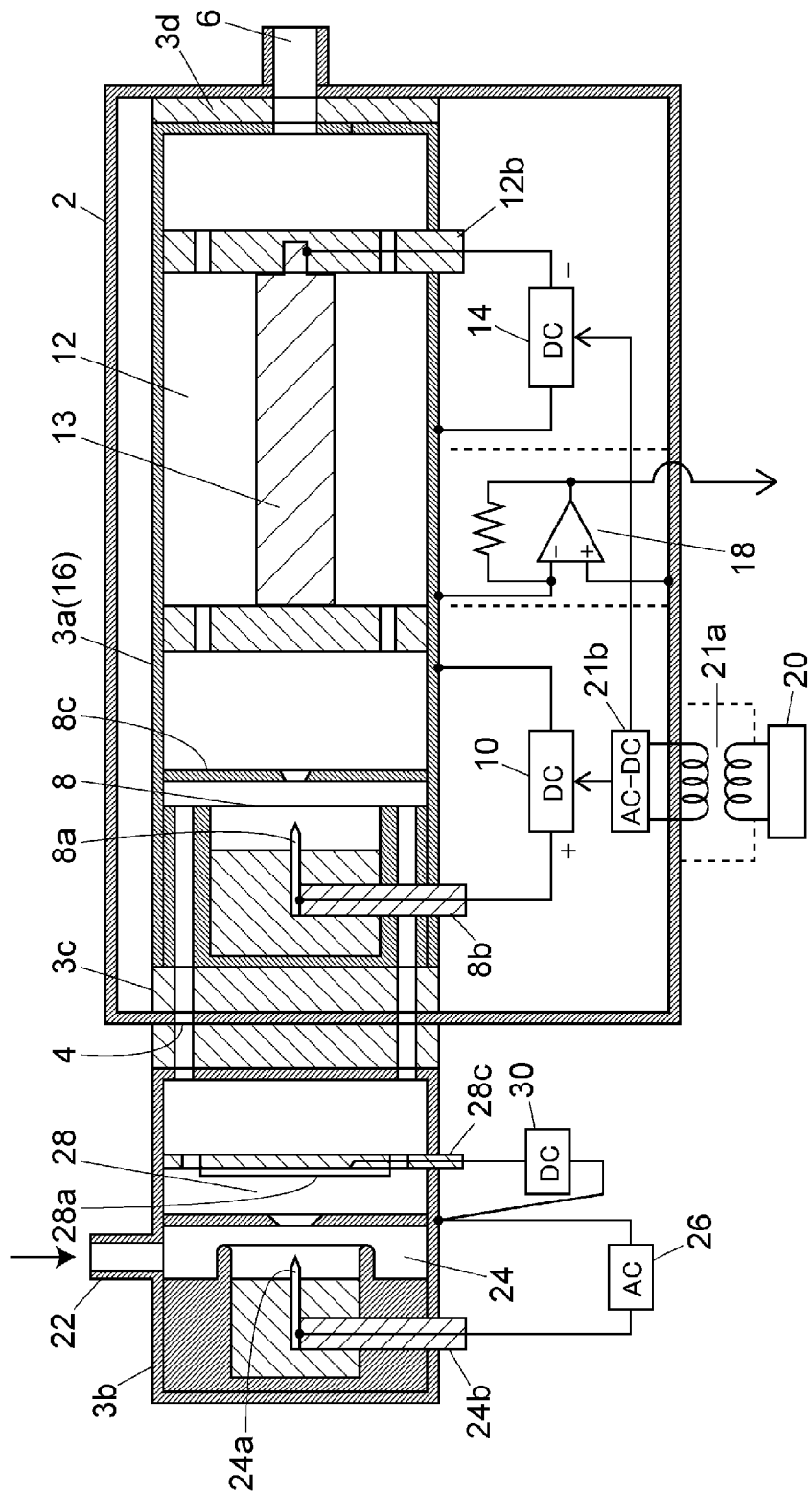
FIG. 3 is a diagram concretely showing the embodiment, and shows a cross-sectional diagram of a flow path along a flowing direction together with a circuit diagram.

FIG. 3 shows an example of a concrete configuration of the present embodiment. The flow paths 3a and 3b are cylindrical and are formed of conductive material, and are joined by the insulating member 3c, but are electrically separated from each other. The flow path 3b is grounded.

The flow path 3b is a preprocessing section. One end of the flow path 3b is closed, and the discharge neutralizer 24 is arranged on the side of this end portion, and on the side of the flow path 3a, the ion trap 28 is arranged being adjacent to the neutralizer 24. The aerosol supply port 22 through which an aerosol is supplied is provided with the neutralizer 24, and the electrode 24a for neutralization by AC corona discharge is arranged inside the neutralizer 24. The electrode 24a is insulated from the flow path 3b by the insulating member 24b, and is connected to the AC high-voltage power supply 26.

The neutralizer 24 and the ion trap 28 are linked through an opening provided at a position facing the electrode 24a of the neutralizer 24, and the ion trap electrode 28a having an area greater than the opening is arranged inside the ion trap 28, at a position facing the opening. The ion trap electrode 28a is insulated from the flow path 3b by the insulating member 28c, and is connected to the DC power supply 30. At the ion trap 28, the flow path 3b, which is grounded, is the other electrode of the ion trap 28. An electric field for the ion trap is applied between the electrode 28a and the flow path 3b. An aerosol neutralized by the neutralizer 24 is led into the ion trap 28 through the opening, and comes into contact with the electrode 28a.

The flow path 3a where the unipolar charging section 8 and the ion trap 12 are arranged is arranged inside the shield electrode 2 formed of conductive material, and the flow path 3a and the shield electrode 2 are insulated by the insulating members 3c and 3d. The shield electrode 2 is grounded, and is formed into a shape of a container covering the flow path 3a. Both the shield electrode 2 and the flow path 3b of the preprocessing section are grounded, and thus, they may be connected while being conducted with each other, but in the present embodiment, they are insulated from each other.

In the present embodiment, the flow path 3a serves also as the guard electrode. The unipolar charging section 8 is arranged inside the flow path 3a, on the side of the preprocessing section, and the electrode 8a is arranged at the center of the unipolar charging section 8, that is, on the center axis of the flow path 3a. The electrode 8a is insulated from the flow path 3a by the insulating member 8b, and is connected to the DC high-voltage power supply 10 arranged on the outside of the flow path 3a. The ion trap 28 and the unipolar charging section 8 are linked by inlet flow paths 4 that are provided passing through the shield electrode 2 and the insulating member 3c. A plurality of inlet flow paths 4 are provided through the wall at the boundary of the ion trap 28 and the unipolar charging section 8, and are circumferentially arranged at regular intervals around the center axis of the flow path 3a. An aerosol from the ion trap 28 is led to the unipolar charging section 8 through the inlet flow paths 4.

A wall 8c formed of conductive material is provided at the boundary of the unipolar charging section 8 and the ion trap 12 on the downstream, and an opening is provided at the center of the wall. The wall 8c is conducted with the flow path 3a, DC high voltage of about several KV is applied between the electrode 8a and the wall 8c by the DC high-voltage power supply 10, and particles in the aerosol led to the unipolar charging section 8 are charged to the positive potential.

The ion trap 12 is provided inside the flow path 3a, adjacent to and on the downstream side of the unipolar charging section 8. The columnar ion trap 13 is arranged in the ion trap 12, on the center axis of the flow path 3a, and the ion trap electrode 13 is insulated from the flow path 3a by an insulating member. The ion trap electrode 13 is connected to the terminal on the negative electrode side of the ion trap power supply 14 arranged outside the flow path 3a, and voltage of about −100 V is applied thereto. The terminal on the positive electrode side of the ion trap power supply 14 is connected to the flow path 3a.

A plurality of through holes are formed in the insulating members supporting the ion trap electrode 13 on the upstream side and the downstream side of the flow path 3a, and the through holes are circumferentially arranged at regular intervals around the center axis of the flow path 3a. The aerosol from the unipolar charging section 8 is led to the ion trap 12 through the through holes on the upstream side. At the ion trap 12, remaining gas ions in the aerosol are drawn to the ion trap electrode 13, and charged particles leaves the ion trap 12 through the through holes on the downstream side without being drawn to the ion trap electrode 13. The outlet 6 is provided downstream of the ion trap 12, through the shield electrode 2.

The conductive materials forming the flow paths 3a and 3b, and the shield electrode 2 may be the same or different. The materials are not particularly restricted, and an appropriate material such as copper, aluminum, stainless steel or the like may be used.

The DC high-voltage power supply 10, the AC-DC converter 21b, the ammeter 18, and the ion trap power supply 14 are arranged between the flow path 3a and the shield electrode 2, and the connection among these and the flow path 3a and the shield electrode 2 is as described above with reference to FIG. 2. The DC high-voltage power supply 10, the AC-DC converter 21b, and the ion trap power supply 14 include a shield function.

Figure 4:
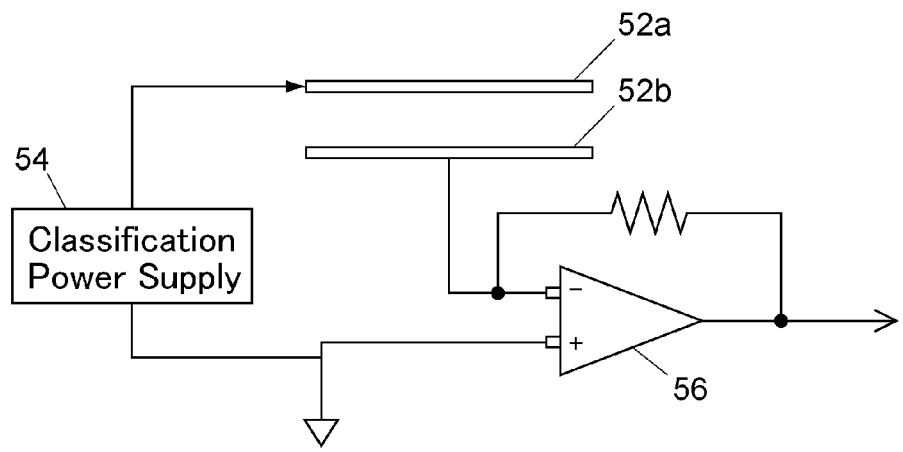
FIG. 4 is a diagram schematically showing a classification section according to another embodiment.

A more preferred embodiment will be described. Classification electrodes 52a and 52b as shown in FIG. 4 may be arranged, instead of the diffusion filter 50, inside the flow path 3, at the position of the diffusion filter 50 shown in FIG. 2, while being electrically insulated from the flow path 3. An electric field that draws charged particles of particle diameters having predetermined electrical mobility is applied between the classification electrodes 52a and 52b by a classification power supply 54. A microammeter 56 including a current-voltage conversion circuit is connected to one of the electrodes 52b, to detect current which has been drawn and flown in. By providing such classification electrodes, charged particles having particle diameters smaller than a certain particle diameter may be captured, and the particle count of particles of the particle diameters captured by the classification electrodes may be measured based on the current value.

Further, another preferred embodiment will be described. According to an embodiment of FIG. 5, charged particles of particle diameters equal to or smaller than a predetermined particle diameter are captured downstream of the outlet 6 of the flow path 3a of the embodiment of FIG. 2. A flow path 3e that is connected to the outlet 6 of the flow path 3a is arranged in a region surrounded by a shield electrode 2a formed of conductive material. The flow path 3e is also formed of conductive material, and serves also as a guard electrode. The shield electrode 2a may be conducted with the shield electrode 2, but the flow path 3e is electrically separated from the flow path 3a. A pair of classification electrodes 60 and 62 is arranged inside the flow path 3e, and a predetermined electric field is applied between the classification electrodes 60 and 62 by the classification power supply 54 in such a way that charged particles having electrical mobility equal to or higher than predetermined electrical mobility are drawn in. The voltage to be applied to the classification electrodes 60 and 62 is set according to the particle diameters of charged particles that are to be drawn in, and is, for example, 1 KV.

To detect current by the charged particles captured by the classification electrodes 60 and 62, a microammeter 56 including a current-voltage conversion circuit is connected between the flow path 3e and the shield electrode 2a. The microammeter 56 is arranged inside the space surrounded by the shield electrode 2a together with the classification power supply 54. A case of the classification power supply 54 is connected to the flow path 3e, to form a part of the guard electrode.

It is schematically shown that power is supplied to the classification power supply 54 by a transformer, but in reality, power is supplied via the same transformer 21a and AC-DC converter 21b as in the case of power supply to the DC high-voltage power supply 10 shown in FIG. 2, or power is supplied by a different but similar transformer and an AC-DC converter.

An operational amplifier with high gain is used for the current-voltage conversion circuit of the microammeter 56, and negative feedback is applied by a resistor that performs current-voltage conversion. The flow path 3e and the shield electrode 2a have approximately the same potential (a potential difference of about 1 mV or less) due to imaginary short of the operational amplifier, and thus, the charge that is accumulated by the electrostatic capacitance between the flow path 3e and the shield electrode 2a is small, and noise caused by the variation in the charge amount is small.

Figure 5:
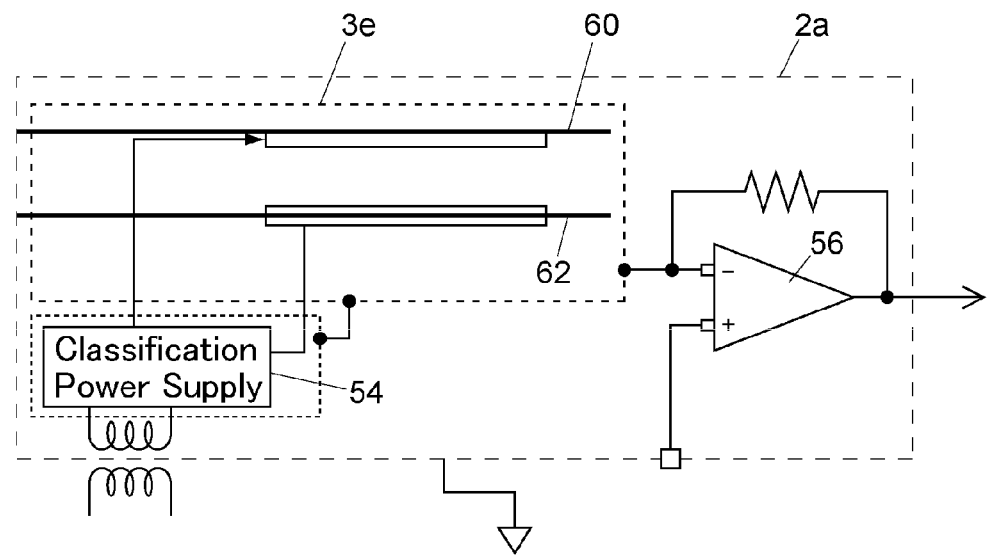
FIG. 5 is a diagram schematically showing a classification section according to another embodiment.

By providing the device according to the embodiment of FIG. 5, the particle count of particles of particle diameters equal to or smaller than a predetermined particle diameter specified by the classification voltage that is applied by the classification power supply 54, or of particle diameters greater than the predetermined particle diameter, among the charged particles which have passed through the particle count measurement device of FIG. 2 or FIG. 3, may be counted.

Figure 6:
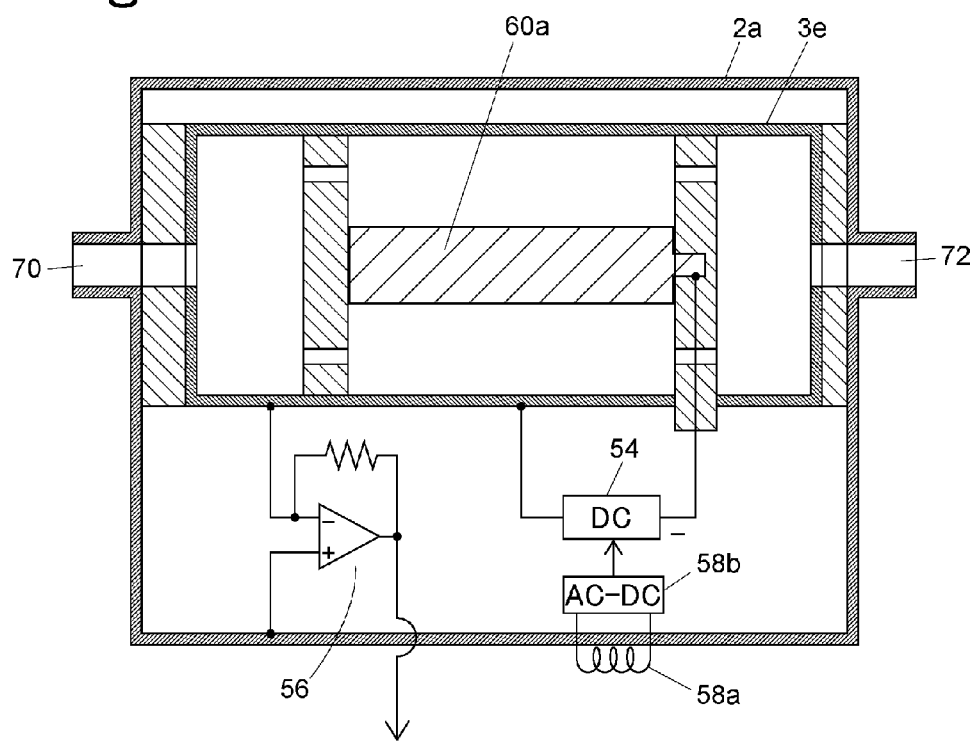
FIG. 6 is a diagram concretely showing the classification section of FIG. 5, and shows a cross-sectional diagram of a flow path along a flowing direction together with a circuit diagram.

FIG. 6 is a concrete example of the device of FIG. 5. The flow path 3e formed of cylindrical conductive material is arranged within the region surrounded by the shield electrode 2a, and the flow path 3e is electrically insulated from the shield electrode 2a by an insulating member. A columnar electrode 60a is arranged inside the flow path 3e, along the center axis of the flow path 3e. The electrode 60a is supported by insulating members at both ends thereof, and is electrically insulated from the flow path 3e. The electrode 60a and the flow path 3e correspond to the classification electrodes 60 and 62 of the device of FIG. 5.

An inlet 70 is provided at one end of the flow path 3e, and an outlet 72 is provided at the other end. The inlet 70 is to be connected to an outlet 16 of the particle count measurement device of FIG. 3, and the shield electrode 2a is conducted with the shield electrode 2 and is grounded by the inlet 70 and the outlet 16 being connected.

A plurality of holes that are circumferentially arranged around the center axis of the flow path 3e are opened to the insulating members supporting both ends of the electrode 60a so that gas including charged particles entering from the inlet 70 flows along the electrode 60a. Gas entering from the inlet 70 enters the space where the electrode 60a is arranged through the holes on the upstream side, and leaves from the outlet 72 through the holes on the downstream side after flowing along the electrode 60a.

The electrode 60a is connected to a negative electrode terminal of the classification power supply 54 through the insulating member, and the flow path 3e is connected to a positive electrode terminal of the classification power supply 54. The classification power supply 54 is arranged in the region surrounded by the shield electrode 2a, and as in FIG. 3, power is supplied to the classification power supply 54 via an AC-DC converter 58b from a secondary side 58a of a transformer. Voltage in a range of, for example, 10 V to 1 KV is applied by the classification power supply 54 to between the electrode 60a and the flow path 3e according to the particle diameters of charged particles to be classified. The classification power supply 54 and the AC-DC converter 58b include a shield function.

The microammeter 56 including a current-voltage converter is connected between the flow path 3e and the shield electrode 2a. The microammeter 56 is also arranged within the region surrounded by the shield electrode 2a.

The charge amount carried in by charged particles captured by the flow path 3e, among the charged particles entering from the inlet 70, is detected by the microammeter 56 as the current value.

The ion trap power supply 14 may also apply voltage to the ion trap electrode 13 in such a way that, in addition to gas ions, charged particles of relatively small particle diameters are also drawn to the ion trap 12. In this case, the particle count concentration of particles having particle diameters in a specific range which is greater than the particle diameters of charged particles to be captured by the ion trap electrode 13 and is smaller than the predetermined particle diameter in the embodiment of FIG. 5 or 6 may be measured.

Figure 7:
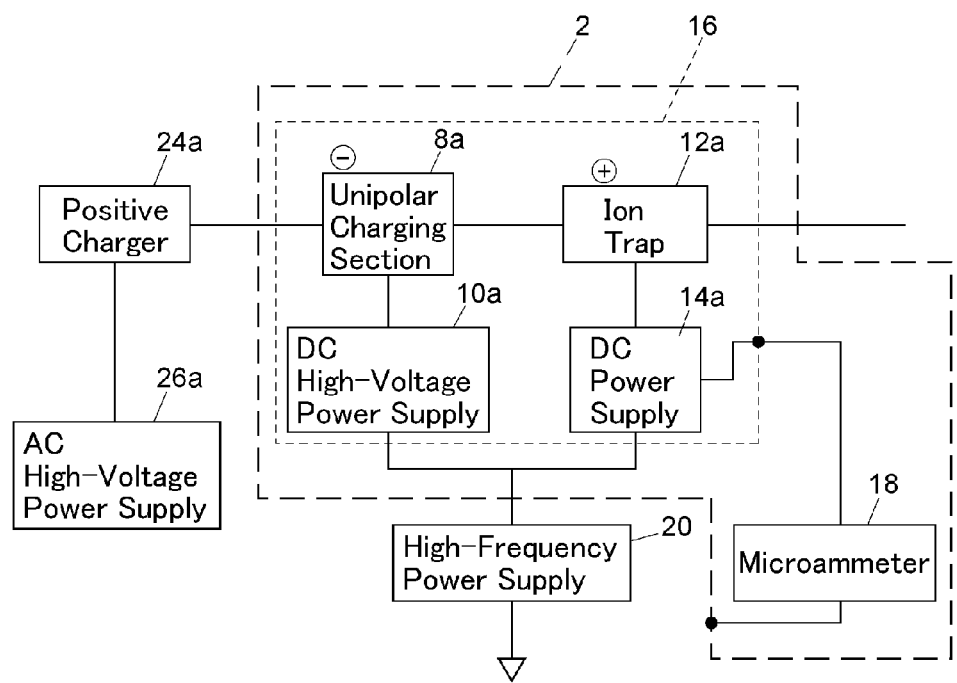
FIG. 7 is a block diagram schematically showing another embodiment.

FIG. 7 is an embodiment of a case where the preprocessing section is a positive charger that performs positive DC discharge. A positive charger 24a receives supply of power of positive 2 KV to 10 KV from a DC high-voltage power supply 26a, and positively charges particles in an aerosol flowing into the measurement region surrounded by the shield electrode 2. The positive charger 24a is, for example, a discharge positive charger based on positive unipolar corona discharge. A unipolar charging section 8a receives supply of power of negative 2 KV to 10 KV from a DC high-voltage power supply 10a, and charges the particles in the aerosol to a negatively charged state. The unipolar charging section 8a is, for example, a discharge negative charger based on negative unipolar corona discharge. An ion trap 12a receives supply of power of positive 1 V to 100 V from a DC power supply 14a, and captures the gas ions in the aerosol.

In the embodiment of FIG. 7, particles in an aerosol flow into the measurement region being positively charged, and flow out of the measurement region being negatively charged, and thus, the particle count concentration is measured based on the charge amount of the difference, and other structures and operations are the same as those of the embodiments of FIGS. 1 and 2.

Figure 8:
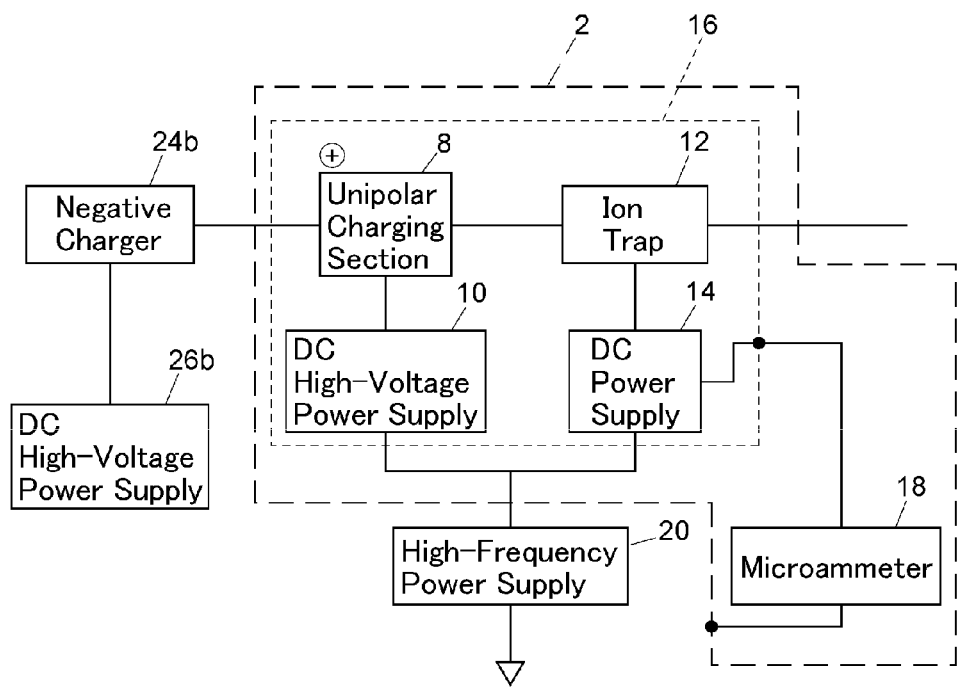
FIG. 8 is a diagram schematically showing another embodiment.

FIG. 8 is an embodiment of a case where the preprocessing section is a positive charger that performs negative DC discharge. A negative charger 24b receives supply of power of negative 2 KV to 10 KV from a DC high-voltage power supply 26b, and negatively charges particles in an aerosol flowing into the measurement region. The negative charger 24b is, for example, a discharge negative charger based on negative unipolar corona discharge. The unipolar charging section 8, the DC high-voltage power supply 10, the ion trap 12, the DC power supply 14, and other structures and operations are the same as those of the embodiments of FIGS. 1 and 2.

In the embodiment of FIG. 8, particles in an aerosol flow into the measurement region being negatively charged, and flow out of the measurement region being positively charged, and thus, the particle count concentration is measured based on the charge amount of the difference.

DESCRIPTION OF REFERENCE SIGNS

2: Shield electrode
8: Unipolar charging section
12: Ion trap
14: DC power supply
16: Guard electrode
18: Microammeter
24: Discharge neutralizer of preprocessing section
24a, 24b: Discharge charger of preprocessing section
30: Vacuum pump of exhaust mechanism
34: Critical orifice of flow rate adjustment section
50: Diffusion filter
52a, 52b: Pair of counter electrodes
54: Classification power supply
56: Classification ammeter

The invention claimed is:

1. A particle count measurement device for measuring a particle count concentration of an aerosol flowing through a measurement region, the particle count measurement device comprising:
a preprocessing section configured to introduce the aerosol into the measurement region in an electrical state of a positively charged state or a negatively charged state;
a unipolar charging section inside the measurement region, the unipolar charging section being configured to place the introduced aerosol in a positively charged state or a negatively charged state that is an electrical state different from at a time of introduction into the measurement region;
an ion trap arranged inside the measurement region, on a downstream of the unipolar charging section in terms of a flow of the aerosol, the ion trap including an ion trap electrode for generating an electric field that draws only gas ions in the aerosol;
an exhaust mechanism outside the measurement region, the exhaust mechanism being configured to discharge the aerosol from the measurement region at a constant flow rate; and
an ammeter for detecting, wherein the ammeter measures a difference between a current value of charged particles entering the unipolar charging section and a current value of charged particles flowing through the unipolar charging section and the ion trap and leaving the ion trap, and wherein the measured values correspond to the particle count concentration.

2. The particle count measurement device according to claim 1,
wherein the preprocessing section is a discharge neutralizer for placing the aerosol in a neutralized state by AC corona discharge, and
wherein the unipolar charging section is a discharge charger based on unipolar corona discharge, the discharge charger including a DC high-voltage power supply and an electrode.

3. The particle count measurement device according to claim 1,
wherein the preprocessing section is a discharge charger for placing the aerosol in an electrical state of a positively charged state or a negatively charged state by DC corona discharge, and
wherein the unipolar charging section is a discharge charger based on unipolar corona discharge, the discharge charger including a DC high-voltage power supply and an electrode.

4. The particle count measurement device according to claim 1, further comprising:
a diffusion filter arranged between the ion trap and an outlet of the measurement region and formed from a conductive mesh for removing charged particles of particle diameters smaller than a predetermined particle diameter,
wherein the ammeter is configured to measure a difference between current supplied by the unipolar charging section and current flowing into the ion trap and the diffusion filter to measure a particle count concentration of particles having particle diameters equal to or greater than the predetermined particle diameter.

5. The particle count measurement device according to claim 1, further comprising:
a pair of counter electrodes arranged between the ion trap and an outlet of the measurement region, the pair of counter electrodes being arranged in parallel with the flow of the aerosol; and
a classification power supply for generating, at the counter electrodes, an electric field for drawing charged particles having particle diameters smaller than a predetermined particle diameter,
wherein the ammeter is configured to measure a difference between current supplied by the unipolar charging section and current flowing into the ion trap and the counter electrodes to measure a particle count concentration of particles having particle diameters equal to or greater than the predetermined particle diameter.

6. The particle count measurement device according claim 1, wherein the exhaust mechanism includes a flow rate adjustment section for making an exhaust flow rate constant.

7. The particle count measurement device according to claim 6, wherein the flow rate adjustment section is a critical orifice.

8. The particle count measurement device according claim 1, further comprising:
a pair of counter electrodes arranged between the ion trap and an outlet of the measurement region, the pair of counter electrodes being arranged in parallel with the flow of the aerosol;
a classification power supply for generating, at the counter electrodes, an electric field for drawing charged particles having particle diameters smaller than a predetermined particle diameter; and a classification ammeter for measuring current flowing into the counter electrodes, wherein the particle count measurement device also measures a particle count concentration of particles having particle diameters smaller than the predetermined particle diameter based on a measurement value of the classification ammeter.

9. The particle count measurement device according to claim 8, wherein voltage is applied to the ion trap electrode of the ion trap so as to generate an electric field that draws not only the gas ions in the aerosol, but also charged particles of particle diameters smaller than the predetermined particle diameter, and wherein the particle count measurement device also measures a particle count concentration of particles having particle diameters greater than particle diameters to be captured by the ion trap and smaller than the predetermined particle diameter based on a measurement value of the classification ammeter.

* * * * *